United States Patent [19]

Bargiotti et al.

[11] 4,393,052
[45] Jul. 12, 1983

[54] ANTITUMOR ANTHRACYCLINE GLYCOSIDES, THEIR PREPARATION, INTERMEDIATES THEREFOR, AND COMPOSITIONS AND USE THEREOF

[75] Inventors: Alberto Bargiotti, Milan; Giuseppe Cassinelli, Voghera; Sergio Penco, Milan; Federico Arcamone, Nerviano; Annamaria Casazza, Milan, all of Italy

[73] Assignee: Farmitalia Carlo Erba S.p.A., Milan, Italy

[21] Appl. No.: 316,058

[22] Filed: Oct. 29, 1981

[30] Foreign Application Priority Data

Nov. 1, 1980 [GB] United Kingdom ............... 8035195

[51] Int. Cl.$^3$ .................... A61K 31/71; C07H 15/22
[52] U.S. Cl. .................................. 424/180; 536/6.4; 536/53; 536/122
[58] Field of Search ............... 536/17 A, 53, 122, 6.4; 424/180

[56] References Cited

U.S. PATENT DOCUMENTS

| 4,020,270 | 4/1977 | Arcamone et al. | 536/17 A |
| 4,039,663 | 8/1977 | Arcamone et al. | 536/122 |
| 4,067,969 | 1/1978 | Penco et al. | 536/122 |
| 4,265,885 | 5/1981 | Bargiotti et al. | 536/53 |
| 4,325,946 | 4/1982 | Bargiotti et al. | 536/17 A |

Primary Examiner—Johnnie R. Brown
Attorney, Agent, or Firm—Berger & Palmer

[57] ABSTRACT

Novel antitumor anthracycline glycosides are prepared by condensing daunomycinone with 2,3,4,6-tetradeoxy-4-C-methylene-3-trifluoroacetamido-L-threo-hexopyranosyl chloride; 2,3,4,6-tetradeoxy-4-C-methylene-3-trifluoroacetamido-L-arabino-hexopyranosyl chloride or 2,3,6-trideoxy-4-C-trifluoroacetamidomethyl-3-trifluoroacetamido-3-O-trifluoroacetyl-L-lyxo-hexopyranosyl chloride.

10 Claims, No Drawings

ANTITUMOR ANTHRACYCLINE GLYCOSIDES, THEIR PREPARATION, INTERMEDIATES THEREFOR, AND COMPOSITIONS AND USE THEREOF

BACKGROUND OF THE INVENTION

1. Field of the Invention

The invention relates to a novel class of anthracycline glycosides, processes for their preparation, pharmaceutical compositions containing them, the use thereof and a certain group of novel intermediates which are aminodeoxy sugar derivatives used in their preparation.

2. Prior Art

Daunorubicin and doxorubicin, of which the compounds of the present invention are derivatives, are both known anthracycline glycosides used in the treatment of certain tumors. In addition, certain of the starting materials used in the present invention are known and described in the patent literature, for example, in U.S. Pat. Nos. 4,112,076; 4,039,663 and British patent application No. 2034707, all of which are owned by the unrecorded assignee hereof.

SUMMARY OF THE INVENTION

In one aspect thereof, the invention provides a novel class of antitumor anthracycline glycosides of the formula I and pharmaceutically acceptable acid addition salts thereof:

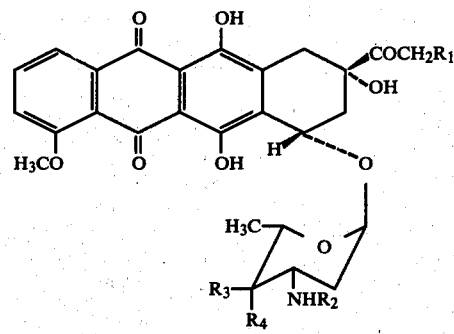

wherein $R_1$ is hydrogen or hydroxy, $R_2$ is hydrogen or acyl, for example, trifluoroacetyl, $R_3$ is methyl, hydroxymethyl, aminomethyl or acylaminomethyl, for example, trifluoroacetylaminomethyl, and $R_4$ is hydrogen or hydroxy, or $R_3$ and $R_4$ together form methylene.

In another aspect thereof, the invention provides a process for the preparation of anthracycline glycosides of the formula I wherein $R_1$ is hydrogen and $R_2$, $R_3$ and $R_4$ are as defined above. According to this aspect of the invention, the process comprises condensing daunomycinone with 2,3,4,6-tetradeoxy-4-C-methylene-3-trifluoroacetamido-L-threo-hexopyranosyl chloride (III-A), 2,3,4,6-tetradeoxy-4-C-methyl-3-trifluoroacetamido-L-arabino-hexopyranosyl chloride (III-B) or 2,3,6-trideoxy-4-C-trifluoroacetamidomethyl-3-trifluoroacetamido-3-0-trifluoroacetyl-L-lyxo-hexopyranosyl chloride (III-C)

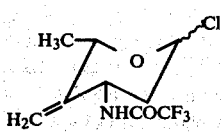

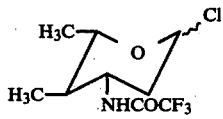

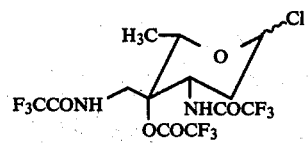

to give respectively, the protected glycosides IV-A (I: $R_1=H$, $R_2=COCF_3$, $R_3+R_4=CH_2$), IV-B (I: $R_1=R_4=H$, $R_2=COCF_3$, $R_3=CH_3$) and IV-C (I: $R_1=H$, $R_2=COCF_3$, $R_3=CH_2—NH—COCF_3$, $R_4=O—CO—CF_3$), and thereafter removing the protecting groups to give respectively the daunorubicin analogues V-A (I: $R_1=R_2=H$, $R_3+R_4=CH_2$), V-B (I: $R_1=R_2=R_4=H$, $R_3=CH_3$) and VC (I: $R_1=R_2=H$, $R_3=CH_2NH_2$, $R_4=OH$). These compounds (V-A, V-B and V-C) are isolated as their hydrochlorides. The condensation of daunomycinone with III-A, III-B or III-C is carried out in the presence of silver trifluoromethanesulphonate as a catalyst, preferably under the conditions described in U.S. Pat. No. 4,112,076.

The corresponding doxorubicin analogues VI-A (I: $R_1=OH$, $R_2=H$, $R_3+R_4=CH_2$), VI-B (I: $R_1=OH$, $R_2=R_4=H$, $R_3=CH_3$) and VI-C (I: $R_1=R_4=OH$, $R_2=H$, $R_3=CH_2NH_2$) are obtained by C-14 bromination followed by hydrolysis of the 14-bromo derivatives, preferably according to the method described in U.S. Pat. No. 4,112,076.

In a still further aspect thereof, the invention provides the novel sugar compounds III-A, III-B and III-C.

In yet a further aspect thereof, the invention provides pharmaceutical compositions comprising a compound of the formula I in admixture with a pharmaceutically acceptable diluent or carrier therefor, as well as methods of using those compounds in treating certain mammalian tumors.

The starting material for the preparation of the intermediates III-A and III-B is methyl 2,3,6-trideoxy-4-C-methyl-3-trifluoroacetamido-α-L-lyxo hexopyranoside (VII), a known compound described in British patent application No. 2034707. Treatment of this compound (VII) in anhydrous benzene with thionyl chloride, followed by aqueous sodium bicarbonate gives methyl 2,3,4,6-tetradeoxy-4-C-methylene-3-trifluoroacetamido-α-L-threohexopyranoside (VIII). Catalytic hydrogenation of compound VIII proceeds stereoselectively giving methyl 2,3,4,6-tetradeoxy-4-C-methyl-3-trifluoroacetamido-α-L-arabino-hexopyranoside (XI). Mild acid hydrolysis of compounds VIII and XI gives the corresponding hexopyranoses IX and XII which by treatment with trifluoroacetic anhydride are transformed into the corresponding 1-0-trifluoroacetates X and XIII. Treatment of these intermediates with dry hydrogen chloride in anhydrous diethyl ether leads to the 1-chloroderivatives III-A and III-B, respectively. The foregoing sequence of transformations is shown in the scheme below:

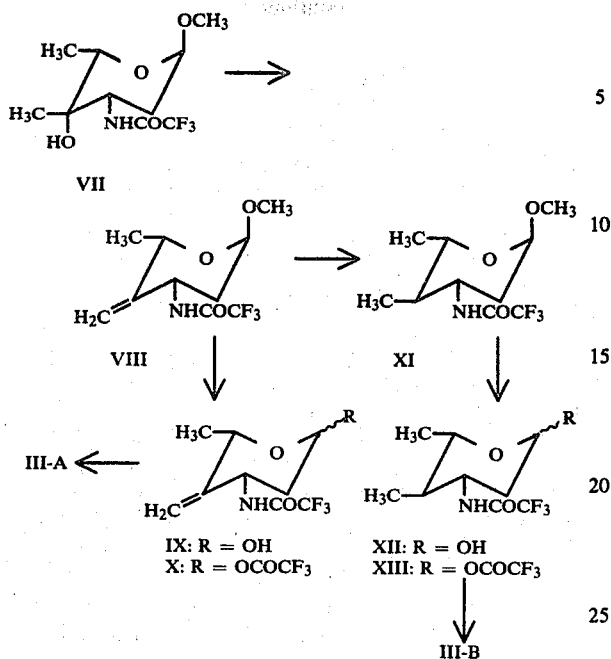

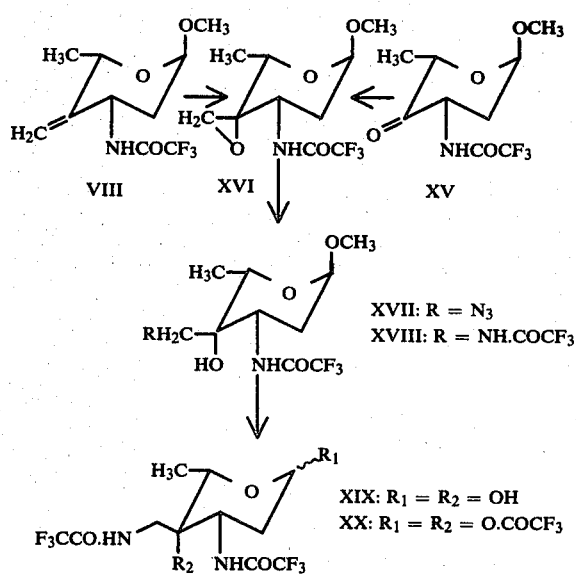

Azidolysis of methyl 2,3,6-trideoxy-4-C-hydroxymethyl-4,4'-anhydro-3-trifluoroacetamido-α-L-lyxo-hexopyranoside (XVI) gives the azido compound XVII. Catalytic hydrogenation thereof, followed by N-trifluoroacetylation affords compound XVIII, which on mild acid hydrolysis gives XIX. Subsequent 0-trifluoroacetylation thereof, followed by treatment with dry hydrogen chloride in anhydrous diethyl ether gives the 1-chloroderivative III-C.

DETAILED DESCRIPTION OF THE INVENTION

The invention will now be described in more detail in conjunction with the following examples of the preparation of the novel compounds of the invention.

EXAMPLE 1

Preparation of methyl 2,3,4,6-tetradeoxy-4-C-methylene-3-trifluoroacetamido-α-L-threo-hexopyranoside (VIII)

A solution of 1 g (3.7 mmol) of methyl 2,3,6-trideoxy-4-C-methyl-3-trifluoroacetamido-α-L-lyxo-hexopyranoside (VII) in 90 ml of anhydrous benzene was treated with 2.75 ml of freshly distilled thionyl chloride and heated under reflux for 2 hours. The reaction mixture, after being cooled to room temperature, was washed with water and then treated under stirring with an aqueous solution of sodium hydrogen carbonate. The organic phase was separated off, washed with water and evaporated under vacuum to dryness to give compound (VIII), 0.82 g, 87% as a white solid; m.p. 160°–162° C., $[\alpha]_D^{20} - 180°$ (c=1, CHCl$_3$). The PMR spectrum (CDCl$_3$) showed absorptions at 1.35 (d, CH$_3$—C—5), 3.37 (s, CH$_3$O), 4.37 (q, H—C—5), 4.83 (broad s, CH$_2$=C—4) and 4.95 δ (broad s, C—1—H).

EXAMPLE 2

Preparation of 2,3,4,6-tetradeoxy-4-C-methylene-3-trifluoroacetamido-L-threo-hexopyranosyl chloride (III-A)

A solution of 0.51 g (2 mmol) of the intermediate VIII in 10 ml of acetic acid and 40 ml of water was heated at 100° C. for two hours, then evaporated to dryness to give 2,3,4,6-tetradeoxy-4-C-methylene-3-trifluoroacetamido-L-threo-hexopyranose (IX, 0.47 g, 99%) as a white solid: m.p. 168°–170° C., $[\alpha]_D^{20} - 160°$ (c=0.5, CHCl$_3$). Treatment of IX (0.36 g, 1.5 mmol) in 25 ml of dry methylene dichloride with 4 ml of trifluoroacetic anhydride for 2 hours at 0° C. and 1 hour at 20° C. gave, after evaporation, the 1-0-trifluoroacetate (X), which was directly used for the preparation of the corresponding 1-chloro-derivative by treatment with dry hydrogen chloride in anhydrous diethyl ether at 0° C. After standing at 0° C. overnight, the reaction mixture was evaporated to dryness to give 2,3,4,6-tetradeoxy-4-C-methylene-3-trifluoroacetamido-L-threo-hexopyranosyl chloride (III-A, 0.35 g, 90%), suitable for the subsequent coupling reaction without further purification.

EXAMPLE 3

Preparation of 4'-deoxy-4'-C-methylene-daunorubicin (V-A)

0.76 g (1.9 mmol) of daunomycinone was condensed with 0.34 g (1.3 mmol) of the protected pyranosyl chloride III-A in 90 ml of dry methylene dichloride in the presence of 6 g of molecular sieves (4 Å-Merck) and using silver trifluoromethanesulphonate (0.45 g, in 15 ml diethyl ether), as catalyst. After 30 minutes under vigorous stirring at room temperature, a saturated aqueous solution of sodium hydrogen carbonate was added to the reaction mixture and the organic phase was separated off, washed with water and evaporated to a small volume. It was then subjected to chromatographic purification on a silica gel column. Elution with a 97:3 by volume chloroform:acetone mixture gave pure 4'-deoxy-4'-C-methylene-N-trifluoroacetyl-daunorubicin (IV-A, 0.66 g, 71%): m.p. 135°–136° C., $[\alpha]_D^{23°} +225°$ (c=0.05, CHCl$_3$). The PMR spectrum (CDCl$_3$) showed absorptions at: 1.42 (d, CH$_3$—C—5'), 2.39 (s, CH$_3$CO), 3.99 (s, CH$_3$O—C—4), 4.60 (q, H—C—5'), 4.95 (m, CH$_2$=C—4'), 5.17 (broad s, H—C—7), 5.52 (broad s, H—C—1'), 13.06 and 13.84 δ (two s, phenolic OHs).

A solution of 0.25 g, 0.4 mmol of IV-A in 10 ml of acetone was treated with 10 ml of 0.2 N aqueous sodium hydroxide and stirred under nitrogen at room temperature. After 3 hours the reaction mixture was adjusted to pH 3.5 with 1 N aqueous hydrogen chloride and extracted with chloroform to eliminate impurities. The subsequent chloroform extraction of the aqueous phase at pH 8, concentration of the organic phase, addition of methanolic hydrogen chloride followed by precipitation with diethyl ether gave 4'-deoxy-4'-C-methylene-daunorubicin (V-A) as the hydrochloride (0.14 g, 61% yield): m.p. 124°–126° C., $[\alpha]_D^{23°} +142°$ (c=0.05, CH$_3$OH).

EXAMPLE 4
Preparation of 2,3,4,6-tetradeoxy-4-C-methyl-3-trifluoroacetamido-L-arabinohexopyranosyl chloride (III-B)

Stereoselective reduction of 0.5 g of the intermediate VIII (prepared as described in Example 1) in 40 ml of methanol in the presence of 0.5 g of 20% palladium on charcoal under a pressure of 20 atmospheres gave, in quantitative yield, methyl 2,3,4,6-tetradeoxy-4-C-methyl-3-trifluoroacetamido-L-arabino-hexopyranoside (XI) as a white solid: m.p. 132°–134° C., $[\alpha]_D^{23°} -82°$ (c=0.5, CHCl$_3$). The PMR spectrum (CDCl$_3$) showed absorptions at: 0.90 (d, CH$_3$—C—4), 1.23 (d, CH$_3$—C—5), 1.26 (m, H—C—4), 3.42 (s, OCH$_3$), 3.70 (dq, H—C—5), 4.20 (m, H—C—3) and 4.87 δ (dd, H—C—1). A solution of 0.385 g, 1.5 mmol of XI in 7 ml of acetic acid and 28 ml of water was heated at 100° C. for two hours and then evaporated to dryness to give, in quantitative yield, 2,3,4,6-tetradeoxy-4-C-methyl-3-trifluoroacetamido-α-L-arabino-hexopyranose (XII) as a white solid: m.p. 158°–159° C., $[\alpha]_D^{23°} -62°$ (c=0.5, CHCl$_3$).

Compound XII (0.245 g, 1 mmol) was converted into the 1-chloroderivative (III-B, 0.26 g, 1 mmol) via the 1-0-trifluoroacetate XIII following the procedure as described in Example 2.

EXAMPLE 5
Preparation of 4'-deoxy-4'-epi-C-methyl-daunorubicin (V-B)

0.5 g, 1 mmol of daunomycinone was condensed with 0.26 g, (1 mmol) of the 1-chloro derivative (III-B), following the procedure described in Example 3, to give the protected glycoside 4'-deoxy-4'-epi-C-methyl-N-trifluoroacetyl-daunorubicin (IV-B, 0.41 g, 66% yield): m.p. 118°–120° C.) with decomposition), $[\alpha]_D^{23°} +271°$ (c=0.05, CHCl$_3$).

The PMR spectrum (CDCl$_3$) showed adsorptions at: 0.97 (d, CH$_3$—C—4'), 1.33 (d, CH$_3$—C—5'), 2.47 (s, COCH$_3$), 4.10 (s, OCH$_3$—C—4), 5.28 (broad s, H—C—7), 5.53 (broad s, H—C—1'), 13.00 and 13.72 δ (two s, phenolic OHs). Removal of the protecting group, as previously described in Example 3, gave 4'-deoxy-4'-epi-C-methyl-daunorubicin (V-B, 90% yield) as its hydrochloride: m.p. 149°–150° C. (with decomposition), $[\alpha]_D^{23°} = +215°$ (c=0.05, CH$_3$OH).

EXAMPLE 6
Preparation of 4'-deoxy-4'-epi-C-methyl-doxorubicin (VI-B)

A solution of 0.53 g (1 mmol) of 4'-deoxy-4'-epi-C-methyl-daunorubicin hydrochloride (V-B), prepared as described in Example 5, in a mixture of 8 ml of anhydrous methanol, 23 ml of dioxan and 0.6 ml of ethyl orthoformate was treated with 2.4 ml of a solution of 1.86 g of bromine in 20 ml of chloroform. After 2 hours at 10° C., the reaction mixture was poured into 180 ml of a 2:1 by volume mixture of diethyl ether:n-hexane. The resultant precipitate, after being filtered off and washed with diethyl ether to remove the acidity, was dissolved in 40 ml of a 1:1 by volume mixture of acetone:0.25 N aqueous hydrogen bromide. After 20 hours at 30° C. the reaction mixture was treated with 0.9 g of sodium formate in 10 ml of water and stirred for 48 hours at 30° C. The reaction mixture was extracted with chloroform in order to remove some lipophilic impurities. The aqueous phase, after being adjusted to pH 7.6 with aqueous sodium hydrogen carbonate, was repeatedly extracted with chloroform. The combined chloroform extracts were dried over anhydrous sodium sulphate and evaporated to a small volume. They were then treated with anhydrous methanolic hydrogen chloride (pH 3.5) and precipitated with an excess of diethyl ether to give the title compound (VI-B) as the hydrochloride.

EXAMPLE 7
Preparation of 2,3,6-trideoxy-4-C-trifluoroacetamidomethyl-3-trifluoroacetamido-3-0-trifluoroacetyl-L-lyxo-hexopyranosyl chloride (III-C)

A solution of 0.51 g (2 mmol) of the intermediate VIII and 0.69 g, 4 mmol of m-chloroperoxybenzoic acid in 20 ml of dry 1,2-dichloroethane was refluxed for two days. The reaction mixture was washed with aqueous sodium hydrogen carbonate and then with water and the organic layer was evaporated to give crystalline methyl 2,3,6-trideoxy-4-C-hydroxymethyl-4,4'-anhydro-3-trifluoroacetamido-L-lyxo-hexopyranoside (XVI, 0.5 g, 92% yield). The PMR spectrum (CDCl$_3$) showed adsorptions at: 1.07 (d, CH$_3$—C—5), 2.69 (dd, OCH$_2$—C—4), 3.42 (s, OCH$_3$), 4.40 (q, H—C—5) and 4.85 δ (broad s, H—C—1).

Compound XVI was also prepared starting from 0.51 g (2 mmol) of methyl 2,3,6-trideoxy-3-trifluoroacetamido-α-L-threo-hexopyranosid-4-ulose (XV) in 10 ml of methanol by treatment with a solution of 0.64 g of diazomethane in 20 ml of methylene dichloride. The reaction mixture was stirred at room temperature overnight and then evaporated to dryness. The crystalline residue (0.5 g, 92% yield) was identical with that obtained by the previously described route.

A solution of 0.54 g (2 mmol) of compound XVI in 15 ml of dioxan and 5 ml of water was treated with 0.95 g of sodium azide and 0.42 g of ammonium chloride, and then stirred under reflux for 4 hours. The organic layer obtained after the addition of chloroform and water was evaporated to dryness to give the crystalline azido derivative XVII (0.62 g in quantitative yield): m.p. 150°–151° C., $[\alpha]_D^{23°} -179°$ (c=1, CHCl$_3$). The I.R. spectrum (film) showed adsorptions at 3,380 (OH) and 2,210 (N₃) cm⁻¹. The PMR spectrum (CDCl₃) showed adsorptions at: 1.23 (d, CH₃—C—5), 3.35 (s, CH₂—C—4), 3.39 (s, OCH₃), 4.08 (q, H—C—5) and 4.76 δ (broad s, H—C—1).

0.47 g (1.5 mmol) of Compound XVII in 20 ml of methanol was hydrogenated in the presence of 0.5 g of 20% palladium on charcoal under a pressure of 10 atmospheres. After removal of the catalyst by filtration, the solution was evaporated to a colorless syrup which was dissolved in 15 ml of anhydrous methylene dichloride and treated with 2 ml of trifluoroacetic anhydride at 0° C. After 30 minutes, the reaction mixture was evaporated to dryness to give methyl 2,3,6-trideoxy-4-C-trifluoroacetamido-methyl-3-trifluoroacetamido-α-L-lyxo-hexopyranoside (XVIII, 0.47 g, 82%): m.p. 165°-166° C., $[\alpha]_D^{23°} -59°$ (c=1, CHCl₃). The PMR spectrum (CDCl₃) showed absorptions at 1.32 (d, CH₃—C—5), 3.36 (s, OCH₃), 3.88 (q, H—C—5) and 4.73 δ (dd, H—C—1).

A solution of 0.38 g (1 mmol) of XVIII in 8 ml of acetic acid and 32 ml of water was heated at 100° C. for three hours, then evaporated to dryness to give compound XIX as a syrup, which was then treated with 3.5 ml of trifluoroacetic anhydride in 20 ml of methylene dichloride in the presence of 0.035 g of dimethylaminopyridine for 16 hours at 10° C. to give the corresponding di-0-trifluoroacetate XX. Subsequent treatment with dry hydrogen chloride at 0° C. in diethyl ether gave the compound III-C, which was used for the next step without further purification.

EXAMPLE 8

Preparation of 4'-C-aminomethyl-daunorubicin (V-C)

0.48 g (1.2 mmol) of daunomycinone was condensed with 0.48 g. (1 mmol) of the protected pyranosyl chloride III-C in 60 ml of anhydrous methylene dichloride in the presence of 5 g of molecular sieve (4 Å Merck) using silver trifluoromethanesulphonate (0.3 g in 10 ml of diethyl ether) as the catalyst. After 30 minutes under vigorous stirring at room temperature, the reaction mixture was treated with a saturated aqueous solution of sodium hydrogen carbonate. The separated organic phase was washed with water and then evaporated to dryness. The solid residue was dissolved in 15 ml of dry methanol and kept for two hours at room temperature. The crude product obtained by evaporating off the solvent was chromatographed on a silica gel column using a 9:1 by volume chloroform:acetone mixture as the eluting agent to give pure 4'-C-trifluoroacetamidomethyl-N-trifluoroacetyl-daunorubicin (IV-C, 0.52 g, 70%): m.p. 125°-127° C., $[\alpha]_D^{23°} +340°$ (c=0.05, CHCl₃) The PMR spectrum (CDCl₃) showed adsorptions at: 1.41 (d, CH₃—C—5'), 2.37 (s, COCH₃), 4.08 (s, CH₃—0—C—4), 5.09 (broad s, H—C—7), 5.42 (broad s, H—C—1'), 13.11 and 13.90 δ (two s, phenolic OHs). Removal of the protecting groups, as previously described in Example 3, gave 4'-C-amino-methyl-daunorubicin (V-C, 71% yield) as the hydrochloride: m.p. 150°-152° C., $[\alpha]_D^{20°} +229°$ (c=0.04 methanol).

EXAMPLE 9

Preparation of 4'-C-aminomethyl-doxorubicin (VI-C)

The 14-bromoderivative of compound V-C (prepared as described in Example 8) was obtained and successively hydroxylated at the 14-position according to the procedure described in Example 6 to give compound (VI-C) as the hydrochloride.

BIOLOGICAL ACTIVITY

On HeLa cells cloning efficiency in vitro, compounds IV-A and V-C were markedly less active than daunorubicin, while compound V-B maintained a high cytotoxic activity as shown in Table 1.

As regards the in vivo tests, preliminary experiments were carried out on P388 ascitic leukemia. The results are shown in Table 2. All the tested compounds exerted considerable antitumor activity; among the three new derivatives, the most interesting is V-C which, at a dose of 200 mg/kg, was more active than daunorubicin.

TABLE 1

Activity on HeLa cells cloning efficiency in vitro. Treatment for 24 hours

| Compound | Dose (ng/ml) | % of controls | ID₅₀ (ng/ml) |
|---|---|---|---|
| Daunorubicin[a] | 12.6 | 36-97-18 | 9-8.3 |
|  | 6.25 | 66-69-57 |  |
|  | 3.12 | 105-100-70 |  |
| (IV-A)[b] | 3200 | 7 | 1600-1300 |
|  | 1600 | 63-29 |  |
|  | 800 | 115-116 |  |
| (V-C) | 1600 | 3.8 | 1000 |
|  | 400 | 141 |  |
|  | 100 | 143 |  |
| (V-B) | 100 | 0 | 7.7 |
|  | 25 | 4 |  |
|  | 6.2 | 54 |  |

[a]Data of 3 experiments
[b]Data of 2 experiments

TABLE 2

Activity against P388 ascitic leukemia. Treatment i.p. on day 1 after tumor inoculation.

| Compound | Dose (mg/kg) | T/C[a] % | Toxicity deaths |
|---|---|---|---|
| Daunorubicin[b] | 2.9 | 170-172-180 | 0/10-0/6-0/10 |
|  | 4.4 | 170-168-185 | 1/10-0/6-0/10 |
|  | 6.6 | 155-168-190 | 6/10-5/5-4/10 |
| (IV-A) | 100 | 110 | 0/5 |
|  | 200 | 110 | 0/5 |
|  | 400 | 130 | 0/3 |
| (V-C) | 50 | 181 | 0/6 |
|  | 100 | 172 | 0/5 |
|  | 200 | 204 | 0/4 |
| (V-B) | 4.4 | 130 | 0/10 |
|  | 6.6 | 140 | 0/10 |
|  | 10.0 | 140 | 0/9 |

[a]Median survival time of treated mice/median survival time of controls, %.
[b]Data of 3 experiments.

Variations and modifications can, of course, be made without departing from the spirit and scope of the invention.

Having thus described our invention what we desire to secure by Letters Patent and hereby claim is:

1. An anthracycline glycoside of the formula I:

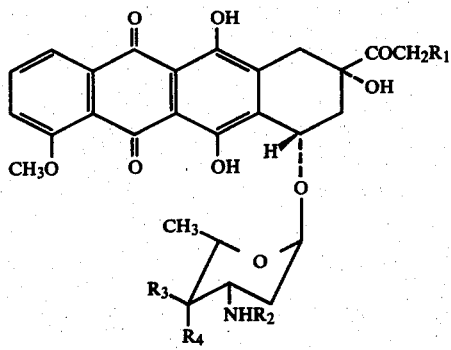

(I)

wherein $R_1$ is hydrogen or hydroxy; $R_2$ is hydrogen or trifluoroacetyl; $R_3$ is methyl, hydroxymethyl, aminomethyl or trifluoroacetylaminomethyl; and $R_4$ is hydrogen or hydroxy, with the proviso that when $R_4$ is hydroxy, $R_3$ is aminomethyl; or $R_3$ and $R_4$ together form methylene, and pharmaceutically acceptable acid addition salts thereof.

2. A compound according to claim 1 wherein the salt is the hydrochloride.

3. A compound according to claim 1 which is 4'-deoxy-4'-C-methylene-daunorubicin hydrochloride.

4. A compound according to claim 1 which is 4'-deoxy-4'-epi-C-methyl-daunorubicin hydrochloride.

5. A compound according to claim 1 which is 4'-deoxy-4'-epi-C-methyl-doxorubicin hydrochloride.

6. A compound according to claim 1 which is 4'-C-aminomethyl-daunorubicin hydrochloride.

7. A compound according to claim 1 which is 4'-C-aminomethyl-doxorubicin hydrochloride.

8. A sugar compound selected from the group consisting of

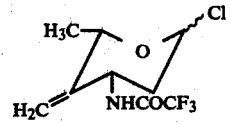

III-A

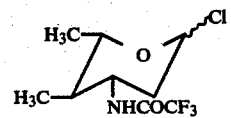

III-B

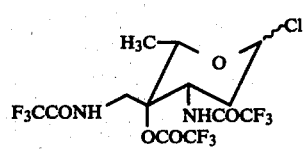

III-C

9. A pharmaceutical composition for treating P388 ascitic leukemia comprising a therapeutically effective amount of a compound according to claim 1 in combination with a carrier therefor.

10. A method of inhibiting the growth of P388 ascitic leukemia comprising administering to a mammal afflicted therewith, a therapeutically effective amount of a compound according to claim 1.

* * * * *